US012623925B2

(12) United States Patent
Chakrabarti

(10) Patent No.: US 12,623,925 B2
(45) Date of Patent: May 12, 2026

(54) EXTRACTIVE DESALINATION OF SEA WATER USING A SPECIAL CLASS OF POLAR ORGANIC SOLVENTS

(71) Applicant: Deven Charles Chakrabarti, Moorestown, NJ (US)

(72) Inventor: Deven Charles Chakrabarti, Moorestown, NJ (US)

(73) Assignee: Deven Charles Chakrabarti, Moorestown, NJ (US)

( * ) Notice: Subject to any disclaimer, the term of this patent is extended or adjusted under 35 U.S.C. 154(b) by 903 days.

(21) Appl. No.: 17/805,321

(22) Filed: Jun. 3, 2022

(65) Prior Publication Data

US 2023/0061678 A1 Mar. 2, 2023

Related U.S. Application Data

(60) Provisional application No. 63/235,224, filed on Aug. 20, 2021.

(51) Int. Cl.

| | |
|---|---|
| ***B01D 11/04*** | (2006.01) |
| ***C02F 1/26*** | (2023.01) |
| ***C07D 207/267*** | (2006.01) |
| *C02F 103/08* | (2006.01) |

(52) U.S. Cl.

CPC .......... *C02F 1/265* (2013.01); *C07D 207/267* (2013.01); *C02F 2103/08* (2013.01); *C02F 2303/16* (2013.01)

(58) Field of Classification Search

CPC . C02F 1/26; C02F 1/265; B01D 11/00; B01D 11/04

See application file for complete search history.

(56) References Cited

U.S. PATENT DOCUMENTS

| | | | |
|---|---|---|---|
| 5,679,254 | A | 10/1997 | Chakrabarti |
| 6,051,111 | A | 4/2000 | Prestidge |

OTHER PUBLICATIONS

Leenheer et al., Anal. Chem. 1987, 59, 1313-1319 (Year: 1987).*

* cited by examiner

*Primary Examiner* — Allison G Fitzsimmons
(74) *Attorney, Agent, or Firm* — Blank Rome LLP

(57) ABSTRACT

A solvent extraction process for desalination of seawater. The process uses a special class of polar organic solvents to preferentially dissolve salt-free water from salty water, which exhibits a reverse solubility-temperature behavior (i.e., the solubility of water in the solvent is high at room temperature but significantly lower at higher temperatures). The desalination process includes adding these special class of solvents to sea or salty water at room temperature, separating the solvent-water phase (organic phase) from the remaining mass of salt-rich water (aqueous phase), heating the solvent-water phase to a higher temperature and recovering the relatively salt-free water that separates out. The process is simple, fast, ecologically safe and energy efficient.

15 Claims, 4 Drawing Sheets

EXTRACTIVE DESALINATION OF SEA WATER USING A SPECIAL CLASS OF POLAR ORGANIC SOLVENTS

This application claims the priority of U.S. Patent Application No. 63/235,224, filed Aug. 20, 2021, which is hereby incorporated by reference.

FIELD OF THE INVENTION

The present invention relates to the desalination of saltwater (such as sea water) using a solvent based extraction process.

BACKGROUND OF THE INVENTION

Fresh water is a staple of life in all regions of the world. We need fresh water for drinking, household purposes, agriculture, husbandry, and industrial use. It is a key determinant of our lifestyle and economic viability of a country. This precious resource is being quickly depleted with global warming and increased extraction of ground water to meet the current demand. According to many scientific studies it is believed that by the end of this century half of the world will suffer from such water scarcity that it will push the world to a breaking point. Though the shortages will hit almost all regions, the less affluent regions will suffer the most. In view of such dire predictions, finding sustainable and inexpensive sources of fresh water has become an urgent global priority.

The problem, as we all know, is not that the world does not have enough water. In fact, 71% of the earth surface is water and most of it is the salty ocean. When saltwater lakes and brackish water are added to the ocean water, about 97.2% of all water on earth is salty. Of the remaining 2.8%, that constitutes fresh water, most of it (2.14%) is locked up in polar ice caps and another 0.61% is stored underground. This leaves a tiny 0.05% to be present in accessible streams, rivers, ponds, freshwater lakes, and aquifers for human consumption.

The problem of availability of fresh water is further aggravated by the fact that this tiny fraction that is fresh water is not necessarily evenly distributed among different regions of the world. Unless an affordable solution to the freshwater problem can be found, many predict that future wars will not be fought over oil but rather on water.

The solution to the problem thus lies on finding affordable desalination processes to seawater to fresh water. Here we use the term seawater to represent a broad range of saline water from high salinity, like those from the ocean containing 35,000 ppm to 40,000 ppm salt, to water of medium salinity, containing 10,000 to 35,000 ppm salt like the ones found in "brackish water" from salt lakes and other inland saline sources.

The problem—desalination—has thus been easy to describe but difficult to solve.

Simply speaking, desalination refers to processes for removing salt from seawater resulting in fresh water for use for human consumption, agriculture, and industrial purposes. Four different technologies—distillation, reverse osmosis, electrodialysis, and freezing—are currently available for this purpose. There are a total of 12,500 desalination plants in operation on a worldwide basis, the users being mostly affluent countries. The largest users of desalination technologies in the world today are the Arab countries (over 70%)—Saudi Arabia, United Arab Emirates, and Kuwait—as well as the United States, Spain and Japan. The technology most in use is reverse osmosis.

Reverse osmosis is the most extensively used. Reverse osmosis is based upon the use of semipermeable membranes which allow water but not dissolved salts to pass. Water is passed at pressures up to 1500 psi across the membrane to generate adequate flow. The energy involved in pumping the water at this pressure, as well as the high capital costs of this technology, result in a high cost solution which only affluent countries can afford.

Distillation involves heating seawater to its boiling point, converting the water into water vapor, and condensing it back to liquid water. The process is very energy intensive, not necessarily because water has to be heated to its boiling point, but because of the large amount of latent heat of evaporation that has to be supplied to convert it into vapor. Improvements involve implementing multiple-effect evaporators, where the heat released during condensation is partially recovered in heating a fresh batch of seawater. Other modifications involve vacuum distillation and multistage flash distillation. In spite of these modifications, distillation remains the costliest approach to desalination.

The freeze-thaw process is generally practiced in arctic regions. In this process, seawater is sprayed under freezing conditions into pads, where the water in its salt-free condition accumulates as ice. When seasons change, and the weather becomes warm, the ice melts to provide fresh water. The process necessarily has regional limitations.

Electrodialysis utilizes electrical potential to remove salts through pairs of charged membranes which trapping salt in alternating channels. Electrodialysis suffers from the same deficiencies of being energy and capital intensive as reverse osmosis and can only be attractive to regions where hydroelectric power is inexpensive and cost competitive.

There are also emerging technologies, such as a chemical extraction method. The method described in U.S. Pat. No. 5,679,254, with variations described in, describe a process for the extraction of salt-free water from seawater using certain non-ionic surfactants. The surfactants used and disclosed in the patent are those that have a relatively low cloud point. Just above their cloud points they extract salt-free water from the seawater. The salt free water remains within the surfactant micelles that constitute the surfactant phase. When this phase is separated and heated much above the cloud point, the salt-free water is released from the surfactant micelles again forming two phases—a relatively water-free surfactant phase and a relatively salt-free water phase. The water phase can then be recovered to provide fresh water for various domestic, industrial and agricultural uses. Though the process is relatively simple and less capital intensive, it never received much commercial interest for the following reasons:

a) Poor space yield. The way a nonionic surfactant phase holds water (above its cloud point) is within their inverted micelles. The cavities of the micelles are relatively small compared to the amount of surfactant surrounding them. Thus, a larger amount of surfactant is necessary to hold a relatively small amount of water, which can be released upon further heating.

b) Slow kinetics of phase separation. The surfactant micelles, being microscopic structures, take a long time to separate from the water phase, particularly at temperatures just above the cloud point, where the water present inside the micelles reduces their specific gravity. Often as long as 24 hours is necessary for a clean phase separation. The rate of phase separation can improve at higher temperature, but as temperature is increased, the amount of water held inside the micelles decreases, thus further decreasing space yield as mentioned above.

c) Difficulty in removing the small amount of surfactant that remains in the recovered desalinated water. Nonionic surfactants are polymeric structures of different chain lengths. As a result, no straight-forward method can be designed to remove all of the surfactants in a single treatment. Furthermore, it is difficult to purify the resulting water sufficiently for drinking purposes, though it may be acceptable for use in agricultural, industrial and other purposes. The surfactant present can result in toxicity and, when ingested, could disturb the biological equilibrium of the body's fluids. Thus, most environmental and public health regulatory authorities have fixed a stringent limit of 0.5 mg/L of nonionic surfactant in drinking water—a limit that is hard to achieve from surfactant-containing water by common purification processes.

If the above deficiencies of the chemical extraction process for desalination of seawater could be solved, it could prove to be a viable, low cost, low capital intensive and universally applicable desalination technology for a wide range of applications.

U.S. Pat. No. 6,051,111 describes a cold distillation method.

SUMMARY OF THE INVENTION

The present invention provides a low-energy, low-cost, low-capital-intensive, easy to operate, regionally non-restrictive, and ecologically safe desalination process by which relatively salt-free water can be extracted from seawater for various domestic, agricultural, and industrial uses.

One embodiment is a method for extracting water from saltwater, the method comprising the steps of:

(a) adding a polar organic solvent to the saltwater to form a mixture, where the polar organic solvent has the following properties:
  (i) dissolves water at or above 10% v/v at room temperature;
  (ii) has a water solubility that decreases with increasing temperature;
  (iii) is liquid at room temperature;
  (iv) has a boiling point above that of water (100° C.) and preferably above 150° C. (or above 160° C.) at standard pressure (760 mm Hg); and
  (v) derives its polarity from one or more groups selected from amide, substituted amide, sulfoxide, sulfone, hydroxyl, and ether groups;

(b) heating the mixture to form a first organic phase and a first aqueous phase; and (c) separating the organic phase from the mixture.

In one embodiment, the mixture is heated in step (b) to no more than about 5° C. above the cloud point of the organic solvent. This is to maximize the amount of water in the first organic phase. In one preferred embodiment, the mixture is heated to about 3 to 5° C. above the cloud point of the organic solvent.

The first organic phase includes the purified water and the organic solvent, while the first aqueous phase contains the removed salt. The first organic phase can be subjected to a second heating step (d) to separate the purified water from the organic solvent. The second heating step results in a second aqueous phase and second organic phase. The second aqueous phase includes the purified water while the second organic phase includes the organic solvent. In a further step (e), the second aqueous phase can be separated from the second organic phase. The separated organic solvent in the second organic phase can be recycled and used with other saltwater when performing step (a) in the next cycle.

Yet another embodiment is a composition comprising (a) saltwater, and (b) a polar organic solvent, where the polar organic solvent has the following properties:

(i) dissolves water at or above 10% v/v at room temperature;
(ii) has a water solubility that decreases with increasing temperature;
(iii) is liquid at room temperature;
(iv) has a boiling point above that of water and preferably above 150° C. (or above 160° C.) at 760 mm Hg; and
(v) derives its polarity from one or more groups selected from amide, substituted amide, sulfoxide, sulfone, hydroxyl, and ether groups, wherein the ratio of saltwater to solvent is about 1:0.01 to about 1:1.

BRIEF DESCRIPTION OF THE DRAWINGS

The present invention will be better understood with reference to the following description taken in combination with the drawings.

DETAILED DESCRIPTION OF THE INVENTION

Figure 1:
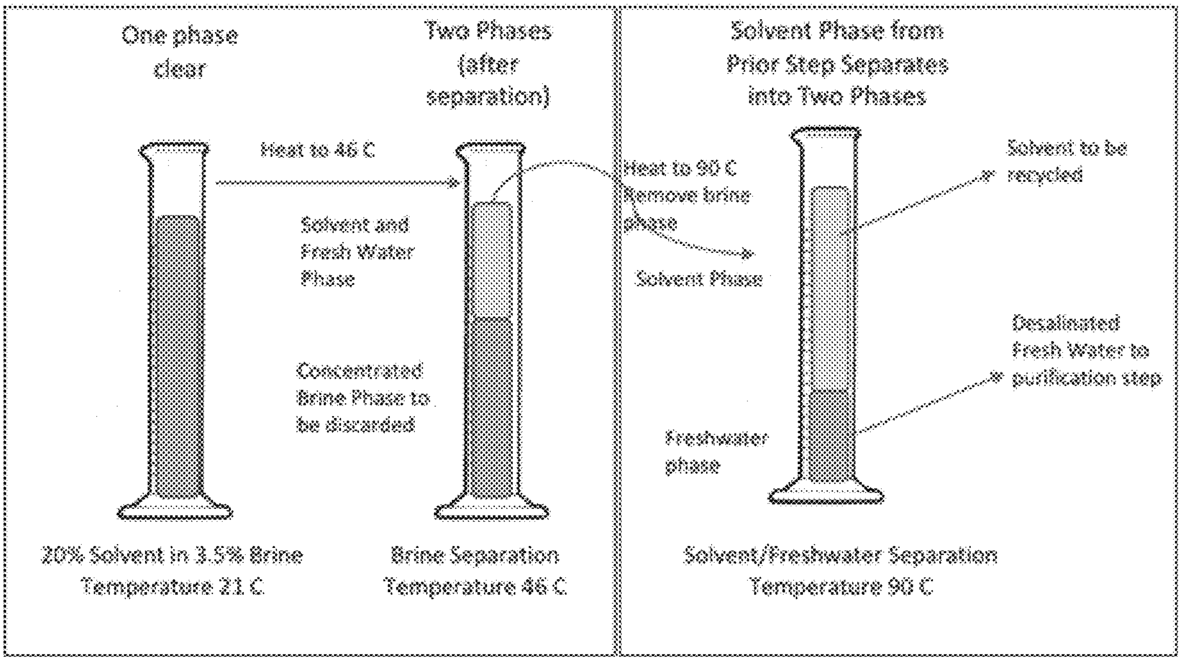
FIG. 1 illustrates an overview of a process for desalination in accordance with the the present invention.

The present inventors discovered a special class of polar organic solvents suitable for extracting water relatively free of salt from saltwater (e.g., seawater) and then recovering the water by a simple differential heat treatment. Optionally, secondary processes can be used to further purity the water. The present invention provides an inexpensive, non-energy/non-capital intensive and simple process for desalination to generate potable water from saline water. The saline water can be sourced from the oceans or from brackish water within continents.

Importantly, the process of the invention does not require the use of expensive membranes, nor does it require sophisticated equipment. Energy requirement is also minimal, for there is no forcing of liquids through resistive membranes, nor is there a need for energy-intensive latent heats of evaporation. Furthermore, unlike chemical extraction processes described in the past, such as described in U.S. Pat. No. 5,679,254, the present invention circumvents the limitations of prior chemical extraction processes. The process of the present invention improves upon prior techniques by using a solvent that has much faster separation kinetics, providing excellent desalination efficiency and allowing for simple removal of the remaining solvent, which is essential for potable water supply.

The desalination process of the present invention capitalizes on the phenomena that the cloud point (namely, the temperature at which phase separation between predominantly water phase and predominantly organic phase starts)

drops when pure water is substituted by saltwater in the solvent water mixture of the present invention. The process starts with the onset of a two phase-system consisting of saltwater and a solvent phase containing salt-free water just above the cloud point in a system comprising a mixture of saltwater (e.g., seawater) and the polar organic solvent. This system is allowed to equilibrate. The two phases are separated and the relatively salt-free water within the solvent organic phase is released by heating the latter to a higher temperature, the higher temperature being so chosen to assure maximum release. The water thus released from the solvent is separated from the newly formed two phases. This water may be suitable for many domestic, industrial and agricultural uses without further treatment. Optionally, particularly if the water is to be used for drinking purposes, it can be treated by conventional methods that are suitable for removing small quantities of well-defined organic chemicals from water. The process is exemplified by the examples below and complemented by the figures provided herein.

Process for Desalination

One embodiment is a method for extracting water from saltwater, the method comprising the steps of:

(a) adding a polar organic solvent to the saltwater (e.g., seawater) to form a mixture, where the polar organic solvent has the following properties:
  (i) dissolves water at or above 10% v/v at room temperature;
  (ii) has a water solubility that decreases with increasing temperature;
  (iii) is liquid at room temperature (e.g., having a freezing point below 22° C.);
  (iv) has a boiling point above that of water and preferably above 150° C. (or above 160° C.) at 760 mm Hg; and
  (v) derives its polarity from one or more groups selected from amide, substituted amide, sulfoxide, sulfone, hydroxyl, and ether groups;

(b) heating the mixture to form a first organic phase and a first aqueous phase; and (c) separating the aqueous phase from the mixture.

In one embodiment, step (a) is performed at ambient temperature.

The temperature to which the mixture in step (b) will be heated depends on the particular polar organic solvent selected. The temperature is preferably adjusted to cause the mixture to phase separate into a predominantly salt-rich phase and a second relatively salt-free aqueous-organic phase.

In one preferred embodiment, the mixture in step (b) to no more than about 5° C. above the cloud point of the organic solvent.

In another preferred embodiment, the mixture is heated in step (b) to about 3 to 5° C. above the cloud point of the organic solvent. Below is a table of solvents and preferred and more preferred temperature ranges for heating mixtures containing them for step (b).

The cloud point of a mixture can be determined by the method described in U.S. Pat. No. 5,679,254, which is hereby incorporated by reference. The cloud point of a nonionic surfactant solution is the temperature at which the surfactant becomes insoluble and separates out from the solution. The transition point is indicated by the first appearance of cloudiness (phase separation upon heating). The general method of determining cloud points consists of mixing one part (unless otherwise specified) of the surfactant under investigation with 99 parts of water (or brine) and cooling it if necessary (when the cloud point of the mixture is below room temperature) until a clear solution. The solution is then gradually heated with stirring and thermometric monitoring until it turns cloudy. The temperature at this point is noted. The reported cloud point is the average of the clouding and clearing temperatures.

| Organic Solvent | Preferred Temperature Range | More Preferred Temperature Range |
|---|---|---|
| Cyclohexyl pyrrolidone | 43-49° C. | 45-47° C. |
| N-dodecyl pyrrolidone | 43-49° C. | 45-47° C. |
| ethylene glycol monobenzyl ether | 43-49° C. | 45-47° C. |
| 2-ethyl-butyl glycol | 43-49° C. | 45-47° C. |
| N-hexyl glycol | 43-49° C. | 45-47° C. |
| 4-methoxy-4-methyl-pentan-2-ol | 43-49° C. | 45-47° C. |

Preferably, step (b) is performed at about 700 to 800 mm Hg, such as at standard pressure (760 mm Hg).

The method for further comprise (d) heating the aqueous phase from step (c) to form a second mixture having a second organic phase and a second aqueous phase and (e) separating the second aqueous phase from the second mixture.

In one embodiment, the ratio of saltwater to solvent is about 1:0.01 to about 1:1. For instance, the ratio of saltwater to solvent may be about 1:0.1 to about 1:1, or about 1:0.5 to about 1:1.

This process may be run in batches or as a continuous system.

The method may further include the step of refining the separated aqueous phase to remove any residual solvent. The refining may be performed by (i) extracting the residual solvent, such as with a hydrocarbon, (ii) absorbing the residual solvent, such as with activated carbon or bentonite clay. For instance, the aqueous phase may be filtered such as through activated carbon or bentonite clay. Removal of the residual solvent can also be achieved by using appropriate molecular sieves. In all the above methods of removal of the residual solvent, both the extracted solvent and the absorbent (except for bentonite clay) can be recovered and/or regenerated and reused.

The process may be used on saltwater having about 1,000 to about 40,000 ppm salt, including on ocean water having a salt content of about 35,000 to about 40,000 ppm and water of medium salinity, for instance containing about 10,000 to about 35,000 ppm salt such as found in "brackish water" from salt lakes and other inland saline sources.

Polar Organic Solvents

The polar organic solvents may be aromatic, cyclic aliphatic, or acyclic aliphatic. The polar organic solvents are not monomers and do not form with themselves of other monomers to form polymeric materials. The polar organic solvent may be non-reactive. The polar organic solvent may be a polar hydrocarbon solvent. The polar organic solvent may have, in addition of hydrogen atoms, oxygen, nitrogen, sulfur or a combination thereof attached to the carbon atoms in the molecule. In addition or alternatively, the polar organic solvent may have one or more polar atoms or groups, such as those selected from halogen, nitro, and ester. In a preferred embodiment, the polar organic is soluble in water at ambient temperature. Solubility of water in the polar organic solvent can be partial or total depending on temperature. Furthermore, the solvents that are preferable in the present invention are those rare molecules that show reverse solubility for water. By reverse solubility of water, in the preferred solvents, we mean that solubility of water in these solvents decreases with increasing temperature. This is a counter-intuitive phenomenon because, according to common experience, solubility of a solute in a solvent increases with increasing temperature. It is rare to find examples where solubility of a solute in a solvent decreases with increasing temperature.

Polarity of a solvent is the ability to form two opposite electrically charged centers in the molecule. The concept is used to describe their dissolving capabilities or interactive forces between solvent and solute (such as water). Because polarity depends on dipole moment, hydrogen bonding, entropy, and enthalpy, it is a composite property without a physical definition. The dipole moment has the greatest influence on polar properties of solvents. Highly symmetrical molecules like benzene, and aliphatic hydrocarbons like hexane, have no dipole moment and are considered non-polar. Alcohols, amides, ethers, esters, ketones, sulfoxides, and sulfones are examples of compounds having a dipole moment.

Solubility of a substance in a solvent is caused by physicochemical interaction between the solvent and solute molecules. One simple way of describing this interaction is by using a donor acceptor concept. This concept applies particularly well with solutes that are themselves polar molecules (in certain embodiments, water) and are dissolved in polar solvents. In this framework, interaction of the polar solvents with solutes occur through interaction of their polar ends—either the positive or the negative or both ends of the dipole of the solvent—with opposing ends of the solute. In case of interaction between water and polar organic solvents, it is to be remembered that one may look at both of these compounds as either solvent or the solute.

In another consideration, interaction between a solvent and a solute is a complex phenomenon. In this way of thinking, in addition to various electronic interactions of which enthalpy of the system is a dominant part, opposite entropic (interaction defying randomness) effects play important roles. The relative roles of these effects often determine the exact nature of the phenomenon of solubility. Higher temperatures are conducive to entropic contributions. In most of our common experiences, we find that solubility of a solute in a solvent increases with increasing temperature; this is primarily due to entropic effect. To see the opposite effect, namely, where solubility decreases with increasing temperature, the entropic effects are overpowered by the other opposing effects (among them enthalpic effects), is not very common. Solvents of the present invention belong to this rare class.

Still another rule of solubility is "like dissolves the like". Water itself being a highly polar molecule can dissolve only in those organic solvents that are themselves polar in nature. But when the solvent is highly polar, such as ethanol, or acetone, it may not be of interest since water and these highly polar solvents are miscible with one another in all proportions at all temperatures. What is important is partial solubility, and in the case of total solubility at room temperature, at least partial solubility at higher temperatures.

Additionally, useful to the present invention are solvents that are non-toxic, and also preferably a non-viscous liquid at room temperature; namely, at the temperatures they will encounter natural seawater; would be non-volatile, i.e., should have high boiling points, preferably having boiling points above 150° C. under atmospheric pressure; and they are preferably nonflammable.

Solvents preferable to the present invention can be aromatic or aliphatic. Preferred solvents include, but are not limited to, aliphatic compounds which are either cyclic or acyclic.

Suitable amide solvents include those of the formula (I):

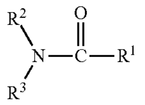

Formula (I)

where $R^1$ is selected from acyclic or cyclic hydrocarbon having 1 to 12 carbon atoms, optionally substituted with one or more of chloro, hydroxy, methoxy, ethoxy, or $—NO_2$; and $R^2$ and $R^3$ are independently selected from hydrogen, acyclic or cyclic hydrocarbon having 1 to 12 carbon atoms, optionally substituted with one or more of chloro, hydroxy, methoxy, ethoxy;

or $R^1$ and $R^2$ can be joined to form a 5- or 6-member ring. The acyclic hydrocarbon can be a straight or branched chain and saturated or unsaturated. The cyclic hydrocarbon can be aromatic or aliphatic. In one embodiment, $R^2$, and $R^3$ are independently selected from straight or branched hydrocarbon chains having a chain length of from 1 to 12 carbon atoms.

Suitable sulfone and sulfoxide solvents include those of the formula (II):

$$R^1—SO_x—R^2 \qquad \text{Formula (II)}$$

where $R^1$ and $R^2$ are independently selected from acyclic or cyclic hydrocarbon having 1 to 12 carbon atoms, optionally substituted with one or more of chloro, hydroxy, methoxy, ethoxy, or $—NO_2$, or $R^1$ and $R^2$ can be joined to form a 5- or 6-member ring; and x is 1 or 2.

Suitable alcohol solvents include those of the formula (III):

$$R^4—OH$$

where $R^4$ is an acyclic or cyclic hydrocarbon having 2 to 12 carbon atoms, optionally substituted with one or more of chloro, $—NO_2$ or $—OR^5$ (where each occurrence of $R^5$ is independently hydrogen, an aliphatic hydrocarbon radical containing from 1 to 8 carbon atoms (e.g., a $C_{1-8}$ alkyl), or an alkyl-aryl radical containing 7 or 8 carbon atoms).

The acyclic hydrocarbon in $R^4$ can be a straight or branched chain. The cyclic hydrocarbon in $R^4$ can be aromatic or aliphatic. For instance, the cyclic hydrocarbon can be a 5- or 6-member ring. In one embodiment, $R^4$ is selected from straight or branched (acyclic) hydrocarbon chains having a chain length of from 2 to 12 carbon atoms. In one embodiment, $R^4$ is aromatic, such as a substituted benzene ring.

The compounds of formulas (I)-(III) should also satisfy the additional physical property requirements that it is a liquid at room temperature, dissolves water at or more than 10% by volume, and in which the water-solubility decreases with increasing temperature.

Preferred polar organic solvents for the methods and composition of the present invention include, but are not limited to, cyclohexyl pyrrolidone (also known as N-cyclohexyl-2-pyrrolidinone or N-cyclohexyl pyrrolidone), N-dodecyl pyrrolidone, ethylene glycol monobenzyl ether, 2-ethyl-butyl glycol, N-hexyl glycol, and 4-methoxy-4-methyl-pentan-2-ol (also known as 4-methoxy-4-methyl-pentanol-2), and any combination of any of the foregoing.

Compositions

The present invention also includes compositions useful for purifying saltwater. One embodiment is a composition comprising (a) saltwater (e.g., seawater), and (b) a polar organic solvent as described herein, wherein the ratio of saltwater to solvent is about 1:0.01 to about 1:1. The polar organic solvent has the following properties:

(i) dissolves water at or above 10% v/v at room temperature;
(ii) has a water solubility that decreases with increasing temperature;
(iii) is liquid at room temperature;
(iv) has a boiling point above that of water and preferably above 150° C. (or above 160° C.) at 760 mm Hg; and
(v) derives its polarity from one or more groups selected from amide, substituted amide, sulfoxide, sulfone, hydroxyl, and ether groups.

In one embodiment, the ratio of saltwater to solvent is about 1:0.01 to about 1:1. In another embodiment, the ratio of saltwater to solvent is about 1:0.1 to about 1:1, or about 1:0.5 to about 1:1. In one embodiment, the solvent is cyclohexyl pyrrolidone. In another embodiment, the solvent is N-dodecyl pyrrolidone. In yet another embodiment, the solvent is ethylene glycol monobenzyl ether. In yet another embodiment, the solvent is 2-ethyl-butyl glycol. In yet another embodiment, the solvent is n-hexyl glycol. In yet another embodiment, the solvent is 4-methoxy-4-methyl-pentan2-ol.

EXAMPLES

Example 1

Figure 2:
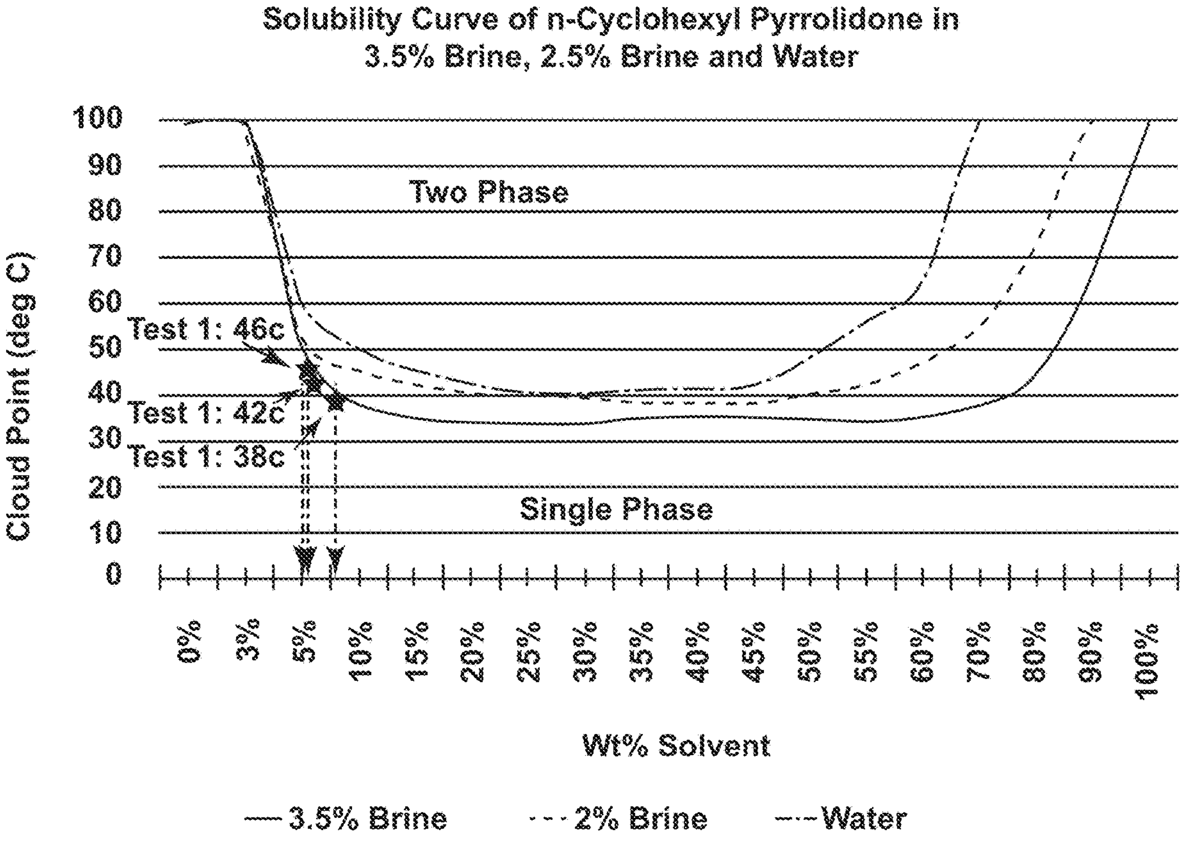
FIG. 2 illustrates a solubility curve of cyclohexyl pyrrolidone in 3.5% brine, 2.5% brine and water.
Figure 3:
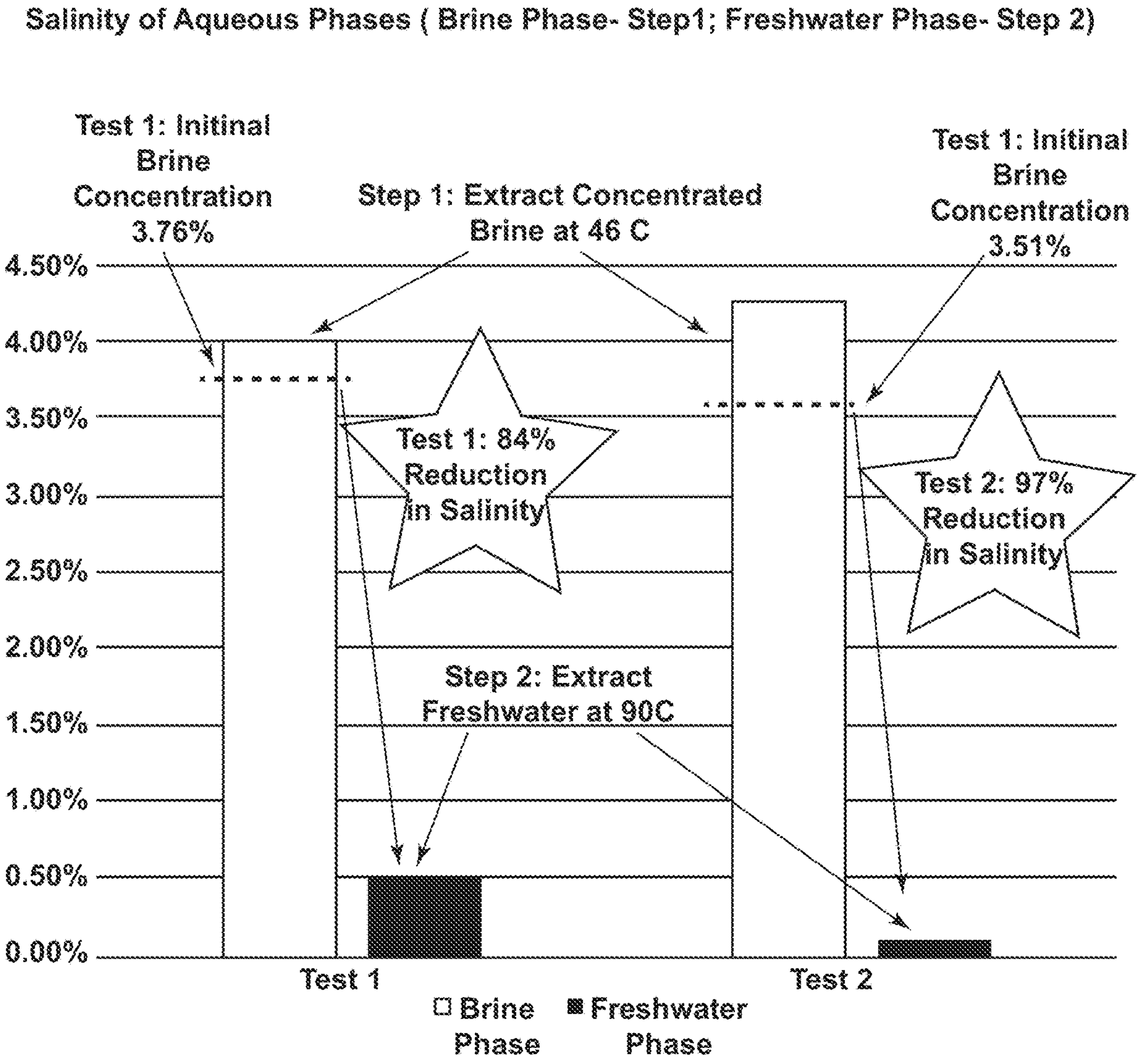
FIG. 3 illustrates salinity of aqueous phases, showing a step 1 brine phase and a Step 2 freshwater phase, in accordance with an embodiment of the present invention.
Figure 4:
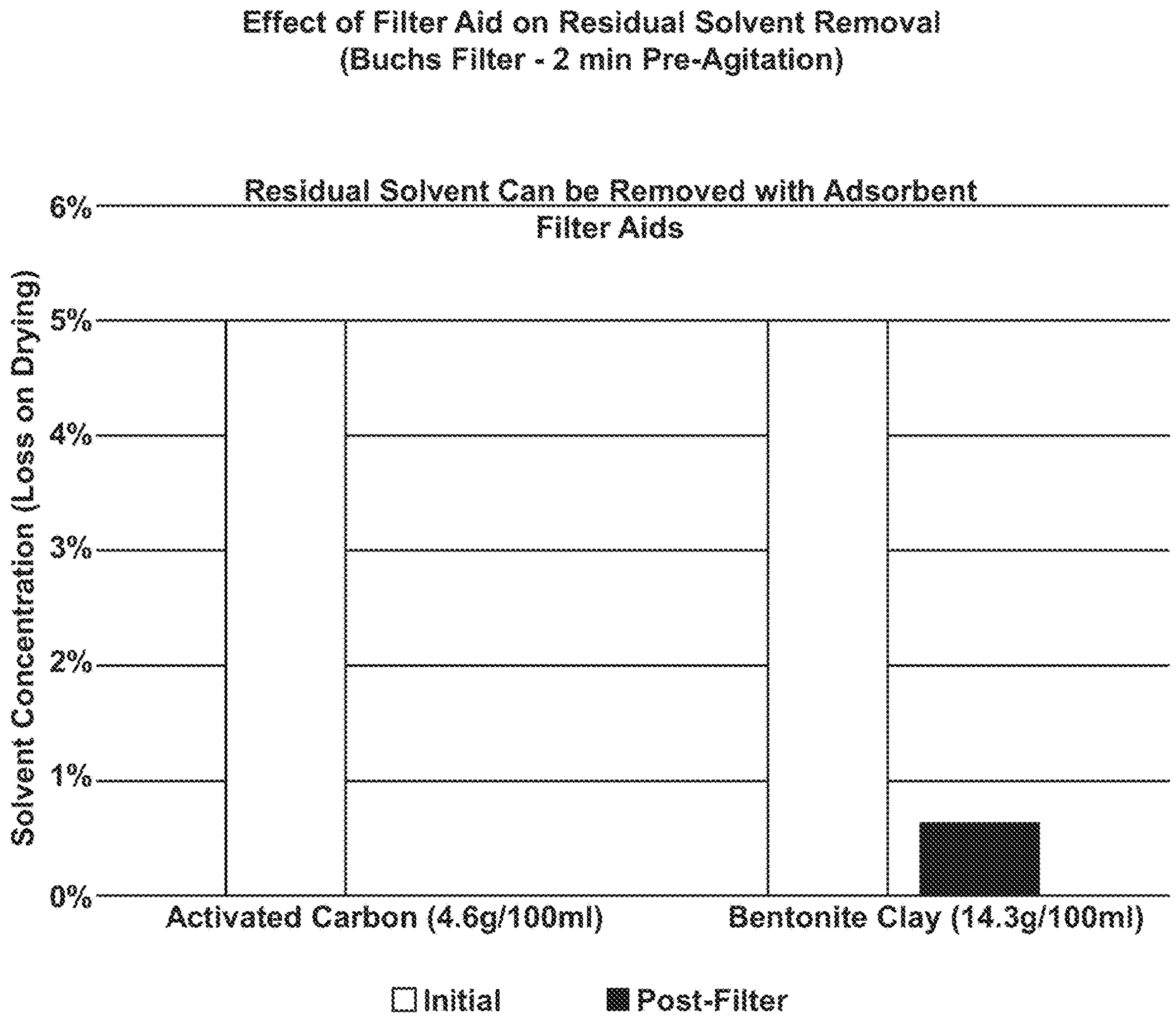
FIG. 4 illustrates the effect of a filter aid (activated carbon or bentonite clay) on residual solvent removal, in accordance with an embodiment of the present invention.

10 ml of N-cyclohexyl pyrrolidone was mixed with 40 ml 3.5% brine solution and heated in a constant temperature water bath to 46° C. After 1 hour the aqueous (lower) phase was removed and measured for salinity using a water quality meter and adjusted using a calibration curve (see FIG. 2). The solvent phase was then raised to 90° C. in a constant temperature water bath at which point the aqueous phase was removed and measured for salinity and solvent concentration. The initial extracted (lower) phase measured a salinity of 4.07%. The final separation of the aqueous (desalinated water) phase yielded a salinity of 0.05% and a solvent concentration of 5%, demonstrating effectively 99.5% desalination.

Example 2

2.8 ml of N-cyclohexyl pyrrolidone was mixed with 11.2 ml 3.5% brine solution and heated in a constant temperature water bath to 46° C. After 1 hour the aqueous (lower) phase was removed and measured for salinity using a water quality meter and adjusted using a calibration curve (see FIG. 2). The lower phase, or initial aqueous phase measured a salinity of 3.96%. On a calculated basis, 98.9% of the NaCl was extracted in this step.

Example 3

2.8 ml of N-cyclohexyl pyrrolidone was mixed with 11.2 ml 3.5% brine solution and heated in a constant temperature water bath to 46° C. After 2 hours the aqueous (lower) phase was removed and measured for salinity using a water quality meter and adjusted using a calibration curve (see FIG. 2). The lower phase, or initial aqueous phase measured a salinity of 4.18%. On a calculated basis, 100% of the NaCl was extracted in this step.

Example 4

2.8 ml of N-cyclohexyl pyrrolidone was mixed with 11.2 ml 3.5% brine solution and heated in a constant temperature water bath to 46° C. After 3 hours the aqueous (lower) phase was removed and measured for salinity using a water quality meter and adjusted using a calibration curve (See FIG. 2). The lower phase, or initial aqueous phase contained 0.417 g of NaCl yielding a salinity of 4.17%. On a calculated basis, 100% of the NaCl was extracted in this step.

Example 5

80 ml of N-cyclohexyl pyrrolidone was mixed with 120 ml 3.5% brine solution and heated in a constant temperature water bath to 46° C. After 3 hours the aqueous (lower) phase was removed and measured for salinity using a water quality meter and adjusted using a calibration curve (see FIG. 2). The solvent phase was then raised to 90° C. in a constant temperature water bath for 2 hours. Afterward the aqueous phase was removed and measured for salinity and solvent concentration. The initial extracted (lower) phase measured a salinity of 4.07%. The final separation of the aqueous (desalinated water) phase yielded a salinity of 0.05% and a solvent concentration of 5%, demonstrating effectively 99.5% desalination.

Example 6

20 ml of N-cyclohexyl pyrrolidone was mixed with 80 ml 3.5% brine solution and heated in a constant temperature water bath to 46° C. After 1 hour the aqueous (lower) phase was removed and measured for salinity using a water quality meter and adjusted using a calibration curve (see FIG. 2). The solvent phase was then raised to 90° C. in a constant temperature water bath for 2 hours. Afterward the aqueous phase was removed and measured for salinity and solvent concentration.

Example 7

20 ml of N-cyclohexyl pyrrolidone was mixed with 80 ml 3.5% brine solution and heated in a constant temperature water bath to 46° C. After 2 hours the aqueous (lower) phase was removed and measured for salinity using a water quality meter and adjusted using a calibration curve (see FIG. 2). The solvent phase was then raised to 90° C. in a constant temperature water bath for 2 hours. Afterward the aqueous phase was removed and measured for salinity and solvent concentration.

Example 8

20 ml of N-cyclohexyl pyrrolidone was mixed with 80 ml 3.5% brine solution and heated in a constant temperature water bath to 46° C. After 3 hours the aqueous (lower) phase was removed and measured for salinity using a water quality meter and adjusted using a calibration curve (see FIG. 2). The solvent phase was then raised to 90° C. in a constant temperature water bath for 2 hours. Afterward the aqueous phase was removed and measured for salinity and solvent concentration.

Examples 9 and 10 exemplify processes for refining an aqueous solution containing the organic solvent with activated charcoal and bentonite clay, respectively.

Example 9

2.5 ml of N-cyclohexyl pyrrolidone was mixed with 47.5 ml of distilled water and 4.6 g of activated charcoal. The solution was vacuumed through a buchs filter twice. The amount of solvent was measured by boiling off the remaining water and weighing the excess material. The loss on drying yield was 0% from an initial concentration of 5%, demonstrating 100% removal of the solvent.

Example 10

2.5 ml of N-cyclohexyl pyrrolidone was mixed with 47.5 ml of distilled water and 14.3 g of bentonite clay. The solution was vacuumed through a buchs filter twice. The amount of solvent was measured by boiling off the remaining water and weighing the excess material.

All references cited herein are hereby incorporated by reference.

What is claimed is:

1. A method for extracting water from saltwater, the method comprising the steps of:

(a) adding a polar organic solvent to the saltwater to form a mixture, where the polar organic solvent has the following properties:

(i) dissolves water at or above 10% v/v at room temperature;

(ii) has a water solubility that decreases with increasing temperature;

(iii) is liquid at room temperature;

(iv) has a boiling point above that of water at a standard pressure (760 mm Hg); and (v) derives its polarity from one or more groups selected from unsubstituted or substituted amide, sulfoxide, sulfone, hydroxyl, and ether groups;

(b) heating the mixture to form a first organic phase and a first aqueous phase; and (c) separating the first organic phase from the mixture, wherein the organic solvent has the formula (I):

Formula (I)

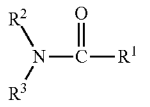

where (a) $R^1$ is selected from acyclic or cyclic hydrocarbon having 1 to 12 carbon atoms, optionally substituted with one or more of chloro, hydroxy, methoxy, ethoxy, or —$NO_2$; and $R^2$ and $R^3$ are independently selected from hydrogen, acyclic or cyclic hydrocarbon having 1 to 12 carbon atoms, optionally substituted with one or more of chloro, hydroxy, methoxy, ethoxy, or —$NO_2$; or (b) $R^1$ and $R^2$ are joined to form a 5- or 6-member ring; and $R^3$ is selected from hydrogen, acyclic or cyclic hydrocarbon having 1 to 12 carbon atoms, optionally substituted with one or more of chloro, hydroxy, methoxy, ethoxy, or —$NO_2$.

2. The method of claim 1, wherein step (a) is performed at ambient temperature.

3. The method of claim 1, wherein the mixture is heated in step (b) to no more than about 5° C. above a cloud point of the organic solvent as determined by mixing one part of the organic solvent in 99 parts of water.

4. The method of claim 1, wherein the mixture is heated in step (b) to about 3 to 5° C. above a cloud point of the organic solvent as determined by mixing one part of the organic solvent in 99 parts of water.

5. The method of claim 1, further comprising (d) heating the first organic phase from step (c) to form a second mixture having a second organic phase and a second aqueous phase and (e) separating the second aqueous phase from the second mixture.

6. The method of claim 1, wherein the saltwater is sea water.

7. The method of claim 1, wherein the mixture has a ratio of saltwater to organic solvent of about 1:0.01 to about 1:1.

8. The method of claim 1, wherein the mixture has a ratio of saltwater to solvent of about 1:0.1 to about 1:1.

9. The method of claim 5, further comprising the step of refining the separated second aqueous phase to remove residual organic solvent.

10. The method of claim 9, wherein the refining step includes one or more of (a) extracting the residual organic solvent with a hydrocarbon or (b) absorbing the residual solvent.

11. The method of claim 1, wherein the polar organic solvent has a boiling point above 150° C.

12. The method of claim 1, wherein the organic solvent includes at least one additional polar group selected from halogen, nitro, and ester.

13. The method of claim 1, wherein the organic solvent has the formula (I):

Formula (I)

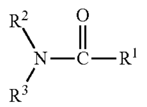

where $R^3$ is independently selected from hydrogen, acyclic or cyclic hydrocarbon having 1 to 12 carbon atoms, optionally substituted with one or more of chloro, hydroxy, methoxy, ethoxy, or —$NO_2$; and $R^1$ and $R^2$ are joined to form a 5- or 6-member ring.

14. The method of claim 1, wherein the organic solvent is cyclohexyl pyrrolidone.

15. The method of claim 1, wherein the organic solvent is N-dodecyl pyrrolidone.

* * * * *